(12) United States Patent
Wen et al.

(10) Patent No.: US 11,696,683 B2
(45) Date of Patent: Jul. 11, 2023

(54) MEDICAL DEVICE SYSTEM

(71) Applicant: International Business Machines Corporation, Armonk, NY (US)

(72) Inventors: Bo Wen, New York, NY (US); Bing Dang, Chappaqua, NY (US); Jeffrey L. Rogers, Briarcliff Manor, NY (US); Duixian Liu, Scarsdale, NY (US)

(73) Assignee: International Business Machines Corporation, Armonk, NY (US)

( * ) Notice: Subject to any disclaimer, the term of this patent is extended or adjusted under 35 U.S.C. 154(b) by 243 days.

(21) Appl. No.: 17/173,181

(22) Filed: Feb. 10, 2021

(65) Prior Publication Data

US 2022/0248958 A1 Aug. 11, 2022

(51) Int. Cl.
*A61B 5/00* (2006.01)
(52) U.S. Cl.
CPC .......... *A61B 5/0024* (2013.01); *A61B 5/0022* (2013.01); *A61B 5/0028* (2013.01);
(Continued)
(58) Field of Classification Search
CPC ... A61B 5/0022; A61B 5/0024; A61B 5/0028; A61B 5/0031; A61B 5/02055;
(Continued)

(56) References Cited

U.S. PATENT DOCUMENTS 6,275,737 B1 8/2001 Mann
7,983,753 B2 7/2011 Severin
(Continued)

FOREIGN PATENT DOCUMENTS

JP 5507470 B2 5/2011

OTHER PUBLICATIONS

Ferguson et al., "Wireless communication with implanted medical devices using the conductive properties of the body." Expert Review of Medical Devices, vol. 8, 4, pp. 427-433, 2011, doi:10.1586/erd.11.16.
(Continued)

*Primary Examiner* — Orlando Bousono
(74) *Attorney, Agent, or Firm* — Kristofer Haggerty; Otterstedt & Kammer PLLC

(57) ABSTRACT

A system for interfacing an in-body medical device with an external network includes a subdermal wideband on-body network (WON) hub, which in turn includes a hub rechargeable battery, a hub processor coupled to the hub rechargeable battery, a device interface configured to communicate with the in-body medical device, and coupled to the hub processor, and a hub-satellite near field communications wireless interface coupled to the hub processor. The system also includes a wearable WON server that in turn includes a server processor, a server-satellite interface coupled to the server processor, and an external network interface coupled to the server processor. The server processor implements a software controller; and a skin-mountable WON tethered satellite that includes a wired satellite-server interface, coupled to the wearable WON server, and a tethered satellite near-field communications (NFC) wireless interface, configured to communicate with the hub-satellite NFC wireless interface, and coupled to the wired satellite-server interface.

12 Claims, 11 Drawing Sheets

(52) U.S. Cl.
CPC .......... *A61B 5/6833* (2013.01); *A61B 5/7225* (2013.01); *A61B 2562/046* (2013.01)

(58) Field of Classification Search
CPC ... A61B 5/1112; A61B 5/1118; A61B 5/6833; A61B 5/7225; A61B 2562/046; H04W 4/80; G16H 40/67; H04B 13/005
See application file for complete search history.

(56) References Cited

U.S. PATENT DOCUMENTS

| | | | |
|---|---|---|---|
| 8,073,541 B2 | 12/2011 | Alt et al. | |
| 8,285,387 B2 | 10/2012 | Utsi et al. | |
| 9,615,399 B2 | 4/2017 | Hong et al. | |
| 2008/0046037 A1 | 2/2008 | Haubrich et al. | |
| 2013/0310664 A1 | 11/2013 | Kozloski et al. | |
| 2014/0300490 A1* | 10/2014 | Kotz .................. | G16H 40/67 340/870.3 |
| 2015/0287960 A1 | 10/2015 | Andry et al. | |
| 2017/0011223 A1 | 1/2017 | Dang et al. | |
| 2017/0095670 A1* | 4/2017 | Ghaffari .............. | G16H 20/30 |
| 2017/0143206 A1* | 5/2017 | Kotz .................. | A61B 5/0205 |
| 2017/0172445 A1 | 6/2017 | Dang et al. | |
| 2017/0347940 A1 | 12/2017 | Carr | |
| 2019/0348209 A1 | 11/2019 | Wen et al. | |

OTHER PUBLICATIONS

Ma et al., "Enabling deep-tissue networking for miniature medical devices." In Proceedings of the 2018 Conference of the ACM Special Interest Group on Data Communication (SIGCOMM '18). ACM, New York, pp. 417-431, 2018. /doi.org/10.1145/3230543.3230566.

Happach et al., "Redundant health care body area network comprising sensor/actuator-network interfaces and offline data evaluation." IP.com Disclosure No. IPCOM000255272D, Publication Date: Sep. 13, 2018.

Segura, Gemstone—A Networkable Implantable Wireless Neurostimulator IMAPS NE Symposium 2018, 12 pages.

Wikimedia Foundation. (Dec. 7, 2020). Body area network. Wikipedia. https://en.wikipedia.org/wiki/Body_area_network.

Wikimedia Foundation. (Dec. 12, 2020). Near-field communication. Wikipedia. https://en.wikipedia.org/wiki/Near-field_communication.

Mell et al., Recommendations of the National Institute of Standards and Technology, Special Publication 800-145, Sep. 2011, 7 pages.

* cited by examiner

MEDICAL DEVICE SYSTEM

BACKGROUND

The present invention relates to the electrical, electronic and computer arts, and more specifically, to medical devices and the like.

An ever-increasing variety of electronic devices, including medical implants, medical wearables, personal electronics, do it yourself (DIY) cyborg devices, and the like, are available to augment the human body. These devices mostly work independent of each other today with little or no intercommunication.

Bluetooth is one of the most widely used technologies for communications among wearable and portable electronic devices. Unfortunately, the 2.4 gigahertz (GHz) frequency of Bluetooth is strongly attenuated by the human body; thus, high power consumption is required to transmit signals from implanted devices. Moreover, Bluetooth has a protocol characterized by a large amount of overhead, which consumes energy and adds time delay to communications, as it is optimized for usage in an uncoordinated environment. This makes Bluetooth unsuitable for certain medical applications that require low latency. Bluetooth also lacks sufficient data bandwidth for some medical applications, such as brain-computer interfaces (BCI). Wi-Fi, near-field communication (NFC), and Zigbee are other common wireless communication technologies. The power consumption of Wi-Fi is too large for battery-powered wearable and implant devices.

Available medical devices include conventional smart badges and patches, which are disposable, flexible devices that provide, for example, for drug release and real-time sensing, often in conjunction with reusable electronic modules. The smart badges and patches are used mostly for a sensing function on skin. Example smart badges and patches for the monitoring and treatment of chronic wounds include pH sensors, heater/thermometer devices, and thermally-activated drug-releasing microbeads. Under-skin sensors are available, but may move under the skin and it may prove difficult to locate the exact position of the sensor. It may also be difficult to provide power to an implanted or injected sensor network, and it may prove difficult to communicate directly between the implanted devices.

SUMMARY

Principles of the invention provide techniques for medical device systems. In one aspect, an exemplary method for processing an input signal from a medical device includes the operations of obtaining the input signal from the medical device; determining if a response action is prescribed in response to the obtained input signal; performing a signal cleanup process and writing resulting data into a database of a wideband on-body network (WON) hub based on the response action not being prescribed in response to the obtained input signal; and determining a status of the response action based on the response action being prescribed in response to the obtained input signal.

In one aspect, a medical system for interfacing at least one in-body medical device with at least one external network comprises: at least one subdermal wideband on-body network (WON) hub, the at least one subdermal wideband on-body network hub comprising a hub rechargeable battery, a hub processor coupled to the hub rechargeable battery, a device interface configured to communicate with the at least one in-body medical device, and coupled to the hub processor, and a hub-satellite near field communications wireless interface coupled to the hub processor. Also included is at least one wearable wideband on-body network (WON) server, the at least one wearable wideband on-body network (WON) server comprising a server processor, a server-satellite interface coupled to the server processor, and an external network interface coupled to the server processor. Additionally, the system includes at least one skin-mountable wideband on-body network (WON) tethered satellite, the at least one skin-mountable wideband on-body network (WON) tethered satellite comprising a wired satellite-server interface (a cable), coupled to the at least one wearable wideband on-body network (WON) server, and a tethered satellite near-field communications wireless interface, configured to communicate with the hub-satellite near field communications wireless interface, and coupled to the wired satellite-server interface. A software controller is implemented on at least one of the subdermal wideband on-body network (WON) hub and the wearable wideband on-body network (WON) server and is configured to monitor and control the at least one in-body medical device.

In one aspect, an on-skin patch comprises a flexible patch substrate; optionally, one or more sensor devices secured to the flexible patch substrate; a hardware processor secured to the flexible patch substrate and configured to obtain information from the one or more sensor devices; a battery secured to the flexible patch substrate and configured to provide power to components of the on-skin patch; one or more radio frequency to direct current (RF-to-DC) converters secured to the flexible patch substrate and configured to convert a received radio frequency signal to a direct current (DC) signal; a voltage converter and a voltage regulator secured to the flexible patch substrate and configured to convert the direct current (DC) signal to a direct current (DC) voltage to charge the battery; and an oscillator and a power amplifier secured to the flexible patch substrate and configured to generate a low-frequency power/data transmission signal.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. For example, one or more embodiments provide one or more of:

a robust wireless power, signal and control mechanism for neuro-physiological sensing and modulation;

orchestration of different methods to achieve efficient communication between medical devices in different parts of the body;

layered architecture that enables devices to connect to a network with an effective and enhanced security communication method;

techniques capable of operation without percutaneous leads (and associated infections) while maintaining high power and high communication bandwidth support for implanted devices and security for sensitive personal bio-information;

continuous streaming of information between medical devices;

smart bandages and patches that act as an energy source for implanted devices and a communication gateway for the implanted devices; and surgery-free maintenance and technology upgrading of smart bandages and patches.

These and other features and advantages of the present invention will become apparent from the following detailed description of illustrative embodiments thereof, which is to be read in connection with the accompanying drawings.

DETAILED DESCRIPTION

Figure 1:
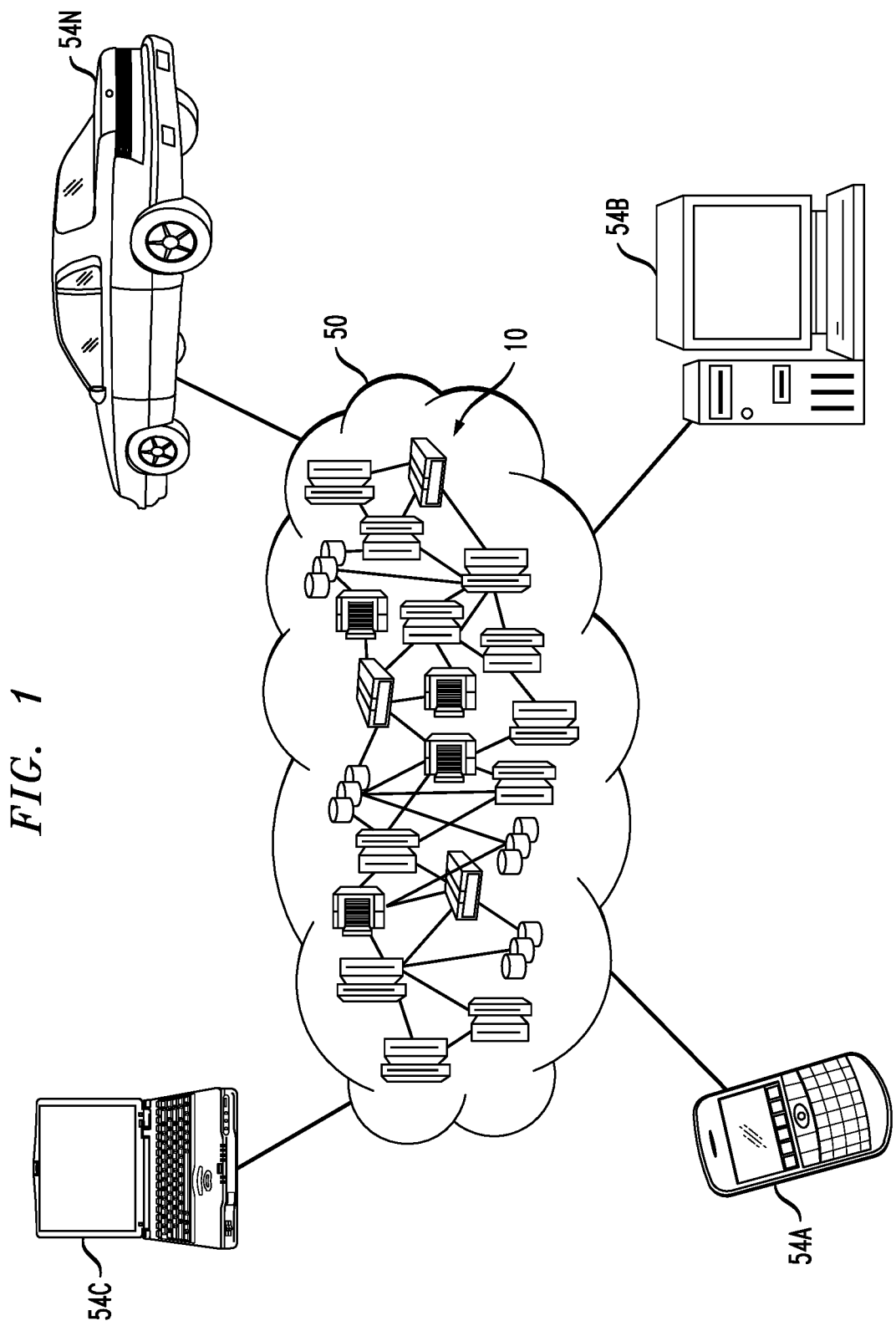
FIG. 1 depicts a cloud computing environment according to an embodiment of the present invention.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
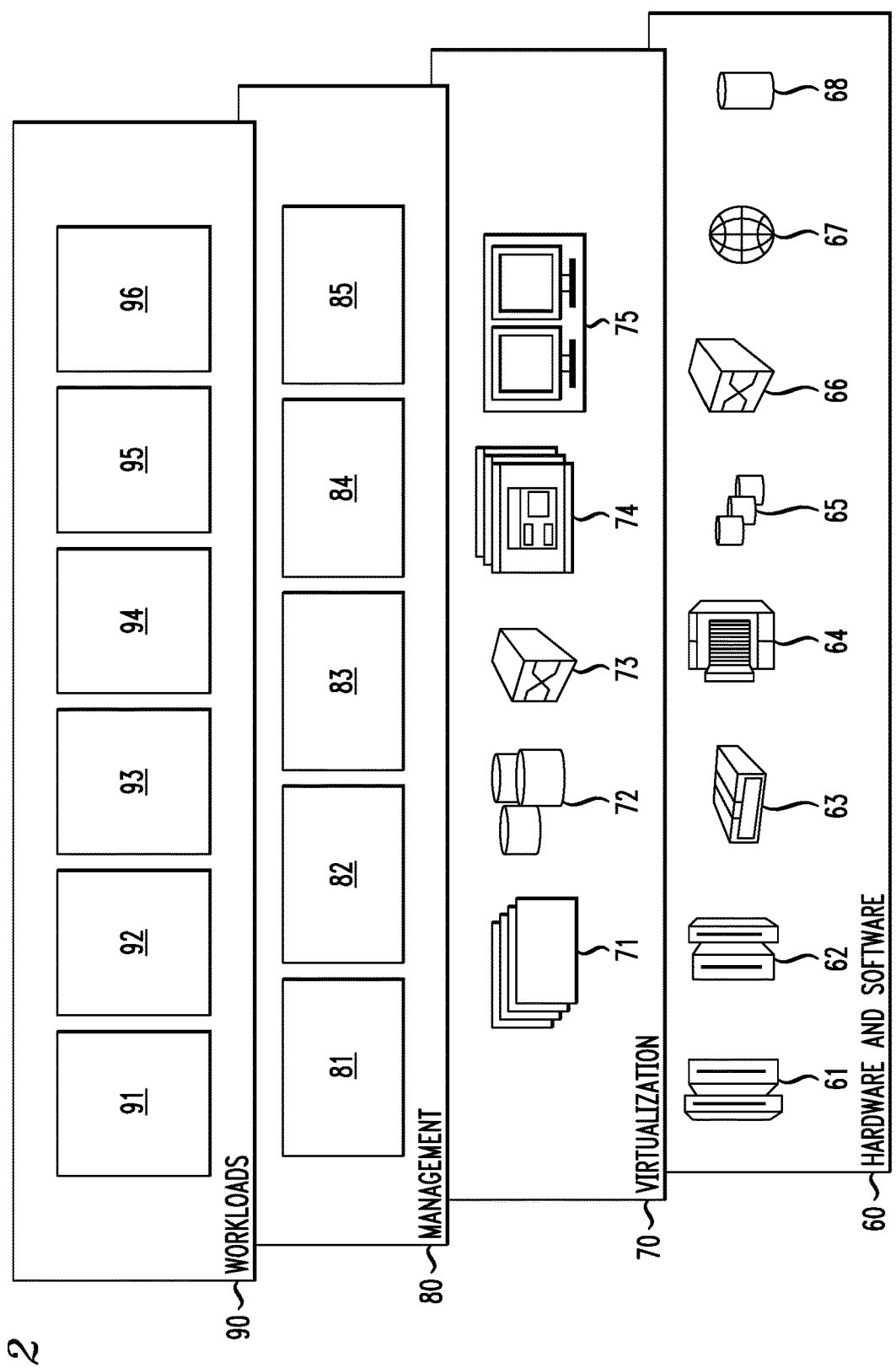
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and a cloud-based medical device manager 96.

Generally, embodiments of a system architecture, medical devices, and a system of medical devices are disclosed. The exemplary system architecture facilitates the interoperability of the medical devices and includes a network (referred to as a body network (BN) herein) for providing communication among wearable, subdermal and implanted devices. In one example embodiment, the BN is a wideband on-body network (WON) utilizing, for example, frequencies as follows: (i) inside body: wired and/or wireless in certain frequency bands (<20 MHz, and 300 MHz to 1 GHz); (ii) subdermal to above skin: near-field wireless technology (<20 MHz, and 300 MHz to 3 GHz); (iii) outside human body: any wireless or wired standard communication protocol. The exemplary system also provides for the integration and inter-communication of off-body systems with networked on-body devices, and with medical devices from a variety of manufacturers.

Out-of-body technologies allow bigger battery form factor and more material choices and, thus, longer battery life and lower engineering and manufacturing cost. Out-of-body technologies can also be replaced easily without a surgical procedure.

In one or more embodiments, the networked devices are configured for coordinated behavior. Examples include brain-machine-interface applications (with the brain signal reading device communicating with an actuator in the arm or leg to perform a body movement) and a pacemaker and insulin pump that coordinate their operation for safety reasons.

In one example embodiments, a medical device includes an on-skin patch that facilitates communication between in-body and out-of-body components. Percutaneous leads or connectors increase the risk of infection; thus, it is preferable for implanted devices to be fully embedded, which means communicating wirelessly, and being powered by a battery or wirelessly. In one example embodiment, a network is utilized to provide data exchange between the devices and to form a functionally integrated system.

Figure 3:
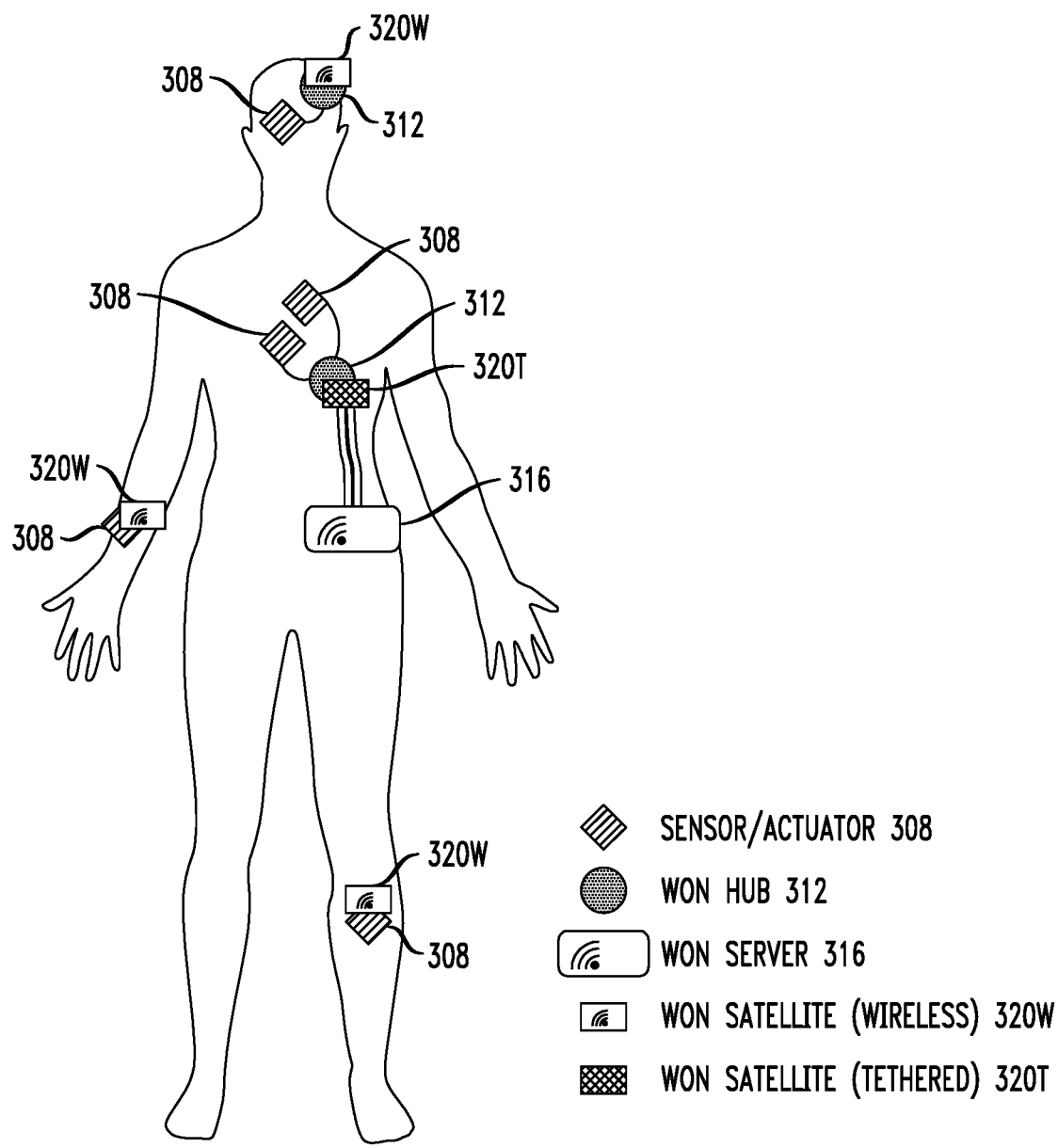
FIG. 3 is a high-level diagram illustrating the position and construction of example medical devices in, on, and nearby the human body, in accordance with an example embodiment.

FIG. 3 is a high-level diagram illustrating the position and construction of example medical devices in, on, and nearby the human body, in accordance with an example embodiment. In one example embodiment, sensor/actuators 308, WON hubs 312, WON servers 316, and WON satellites 320T and 320W are positioned around and/or within the human body.

In one example embodiment, an example on-skin device includes a 3D-printed flexible patch substrate that includes a heater/thermometer device and pH sensor array. A re-usable electronics module reads the sensors, such as the heater/thermometer device and pH sensor array. The re-usable electronics module communicates the obtained information via, for example, Bluetooth communications to a mobile device. A hydrogel layer attached to the 3D-printed flexible patch substrate contains thermally-activated drug-releasing microbeads.

The human body absorbs energy at different rates based, for example, on the corresponding radio frequency. For example, the human body absorbs energy at a relatively high rate in the 30 MHz-200 MHz range and at lower rates under 30 MHz and above 300 MHz. Thus, medical devices planted deep in the human body utilize frequencies under 20 MHz or in the 300 MHz to 1 GHz range. Medical devices implanted closer to the surface of the skin may benefit from the higher data rates of signals in the 1 GHz to 3 GHz range.

Figure 4:
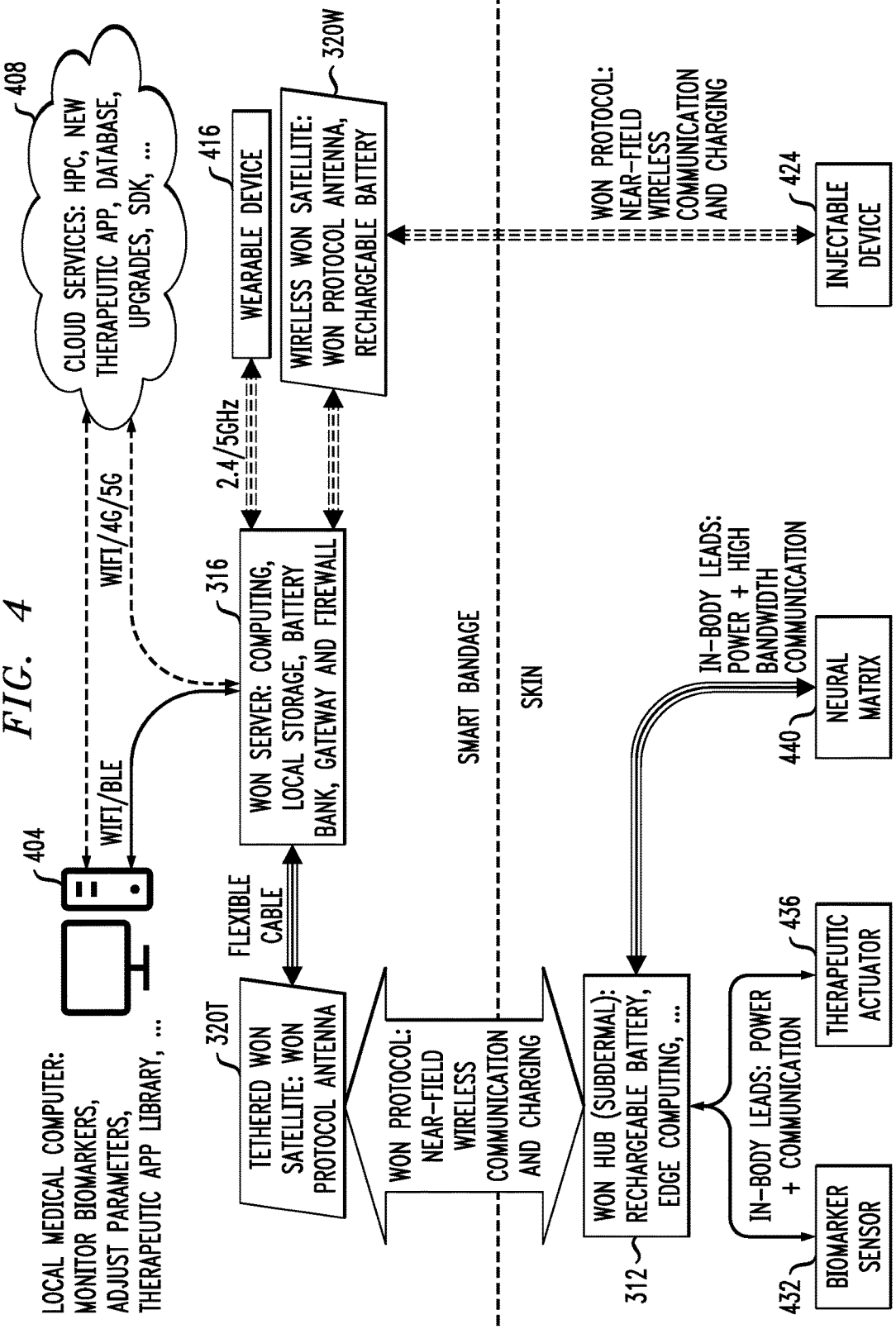
FIG. 4 is a high-level system diagram of an example medical device system, in accordance with an example embodiment.

FIG. 4 is a high-level system diagram of an example medical device system, in accordance with an example embodiment. The exemplary architecture of the medical device system includes four components. A WON Server 316 is a wearable device in the form factor of, for example, a smart phone. It serves as the major computing center of the exemplary "Internet-of-Body" system, providing computing (both artificial intelligence (AI) and classic computing), local data storage, battery bank, internet connectivity, user interface (UI), and the like. It can be upgraded without a surgical operation, so that the system functionality and performance can evolve with technological advancements. In the example, the WON Server 316 also acts as the gateway and firewall between a WON network and external networks, such as a local home/work/hospital network, a cloud infrastructure (including services), and the like. The WON server 316 communicates with local medical computer 404 via, for example, Wi-Fi, Bluetooth Low Energy (BLE), and the like.

The local medical computer 404 performs tasks such as monitoring biomarkers, adjusting parameters, provisioning a therapeutic application library, and the like. The local medical computer 404 and the WON server 316 communicate with cloud services 408 via Wi-Fi, 4G (fourth generation of broadband cellular network technology), 5G (fifth generation of broadband cellular network technology), future cellular generations, and the like. Example cloud services 408 include, but are not limited to, high-performance computing (HPC), therapeutic applications, database services, upgrades, software development kits (SDKs), and the like (see also discussion of element 96 above).

In one example embodiment, the WON server 316 communicates with wearable devices 416 and/or a wireless WON satellite 320W via, for example, 2.4/5 GHz (e.g., Wi-Fi) technology. The wireless WON satellite 320W may be a smart bandage with a WON protocol antenna and a rechargeable battery, for example. The WON server 316 also communicates with tethered WON satellites 320T (via, for example, a flexible cable). In one example embodiment, the wireless WON satellite 320W provides near-field communication and charging for injectable devices 424. (Note that injectable and implantable are used interchangeably herein.)

WON satellites 320W, 320T are, for example, smart bandages or pads that facilitate the communication with subdermal devices, including WON hubs 312 and injectable devices. As they are located outside the human body, they may be removed prior to, for example, undergoing an MRI scan. The WON satellites 320W, 320T can be replaced without a surgical operation; thus, a malfunctioning or damaged unit can be easily replaced. Users can easily purchase newer, upgraded versions to benefit from technology advancements.

WON satellites 320W, 320T are characterized, for example, by form factor:

Wireless WON satellites 320W are battery-powered wireless type devices used to connect with peripheral subdermal devices in the arms, legs, bladder, and other body parts. The wireless WON satellites 320W communicate directly with the subdermal devices via a subdermal WON protocol, then bridge the connections back to the WON server 316 via a wireless WON protocol.

Tethered WON satellites 320T connect directly with the WON server 316 via, for example, a flexible cable and are attached to the skin area directly above the location of the implant of the subdermal WON hub 312. The cable delivers power and high bandwidth communication between the WON server 316 and the WON hub 312.

In one example embodiment, a WON protocol is used to provide near-field wireless communication using a low body absorption frequency to ensure secure, reliable, low power consumption, high data bandwidth communication and charging for, for example, a WON hub 312. The WON hubs 312 are subdermal devices that are connected with one or more implants (deep in-body devices). WON hubs 312 provide common infrastructure functions to support implant operations including, but not limited to, power, communication channels to outside-of-body devices, signal buffering, data compression and encryption, and the like. WON hubs 312 can be packaged on a flexible substrate to allow for better conformance to the human body. WON hubs 312 provide standard communication ports (such as serial peripheral interface (SPI) and/or I$^2$C (Inter-Integrated Circuit)) for implant devices to connect with the network and are a sensor/actuator-agnostic platform. The standard communication ports may also be used to provide power (such as 3.3 volts (V), 5V, and the like). The WON hub 312 includes a rechargeable battery (and thus can support local spinal cord sensing and therapeutic actions even when external components are absent) and provides edge computing for other devices. For example, the WON hub 312 may utilize in-body leads to provide power and communication to a biomarker sensor 432, a therapeutic actuator 436, and the like. The WON hub 312 may also utilize in-body leads to provide power and high bandwidth communication to a neural matrix 440.

Once the signal propagates out of the human body, standard wireless protocols, such as Zigbee, Bluetooth, and the like, form a reliable network without theoretically limiting the number of participants. That is to say, the number of participants can be as many as the standard protocol can support; one or more embodiments do not put any additional limitation on the number of participants.

A WON protocol outlines the communication methods at each level:

For implant devices that are located deep in the body and which require high power and high bandwidth communication, such as a brain or spine neuron matrix, the protocol recommends using flexible ribbon cable or wires to connect with the WON hub 312. If wireless communication is needed, the frequency typically needs to be low (such as below 20 MHz), or 300 MHz to 1 GHz, to avoid human body absorption.

The subdermal WON hub 312 communicates with the WON satellites 320T through the skin and the satellite communicates with the WON server 316. As the WON satellites are placed on the skin opposite the hubs 312, the human body absorption is not a significant problem, so the communication can occur at a higher frequency (such as in the 1 GHz to 3 GHz range) to increase data bandwidth. Security is improved as this is a near-field communication (the transmitter and receiver have to be physically close-by.)

Communications between the WON satellites 320W and the WON server 316 utilize, for example, Bluetooth, Wi-Fi, and various radio frequencies. In one example embodiment, a mesh network is formed to increase robustness. In one example embodiment, the mesh network is a strict local network and the individual sensors do not have direct access to a public network. The WON hub 312 acts as a firewall/gateway between the in-body (implanted) medical devices and the WON network. The WON server 316 acts as a firewall/gateway between the WON network (including the on-body medical devices) and the public network. By using appropriate security on server 316, the control of and data obtained from the individual sensors is protected.

In one example embodiment, the WON hub 312 only communicates with a nearby device (such as a medical device within the same room) for security considerations and does not have long-range communication capabilities. In this embodiment, only data with the explicit consent of the patient and/or caregiver can be transferred into and out of the medical device system (via the WON server 316 which is nearby) and only the consented-to data can be accessed remotely. This reduces the risk of the patient data being compromised.

Figure 5:
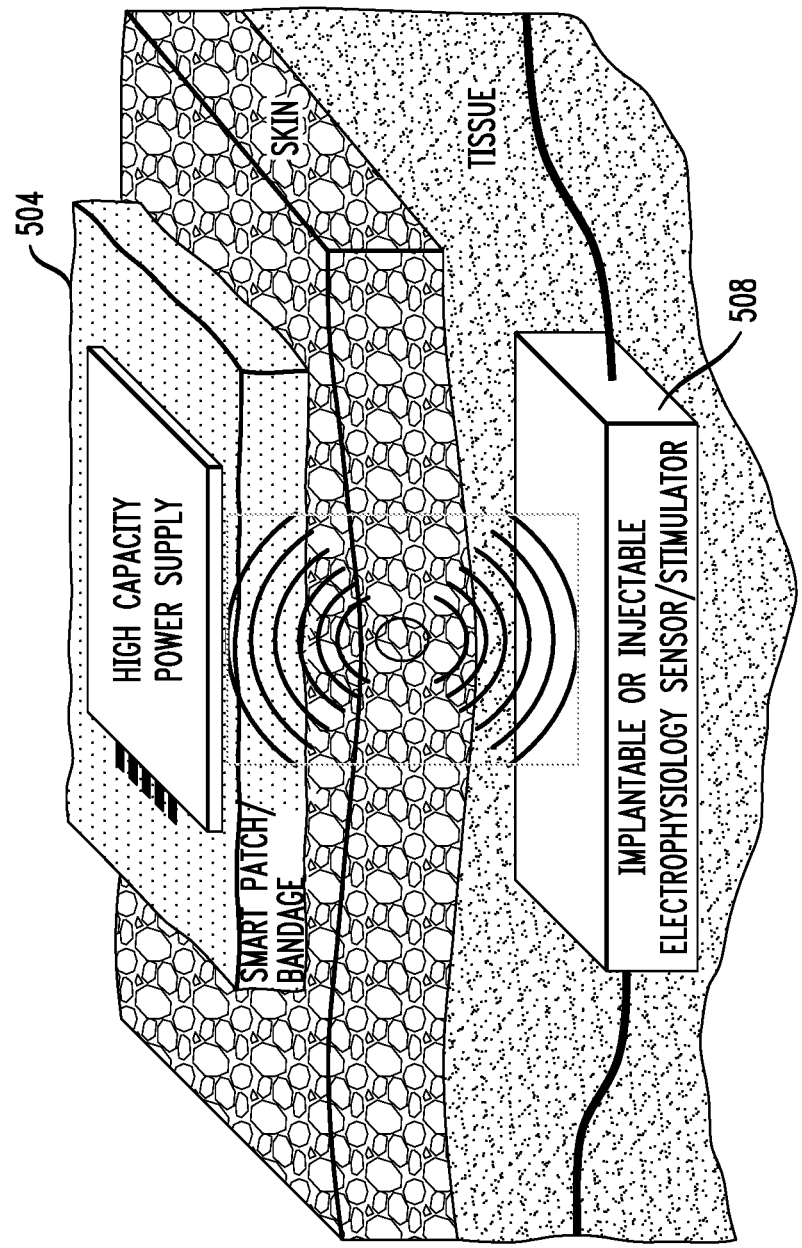
FIG. 5 is a high-level diagram of a smart patch/bandage in communication with an injected or implanted electro-physiological sensor and/or stimulator device, in accordance with an example embodiment.

FIG. 5 is a high-level diagram of a smart patch/bandage 504 in communication with an injected or implanted electrophysiological sensor and/or stimulator device 508, in accordance with an example embodiment. With low-frequency transdermal wireless power and transmission, a smart patch/bandage 504 may be placed above every implantable and injectable neural sensor and/or stimulator device 508.

Figure 6:
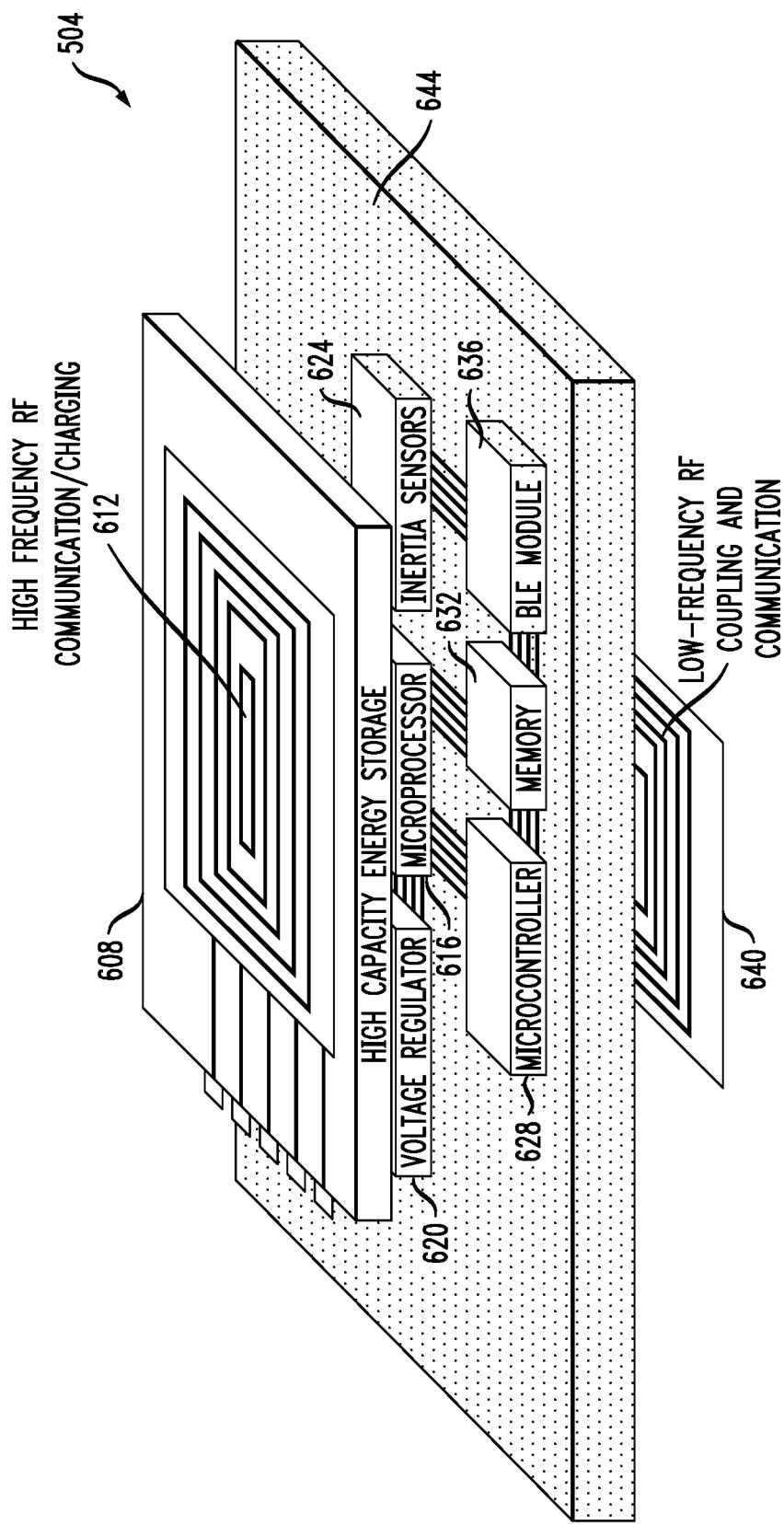
FIG. 6 is a mid-level diagram of the smart patch/bandage, in accordance with an example embodiment.

FIG. 6 is a mid-level diagram of the smart patch/bandage 504, in accordance with an example embodiment. In one example embodiment, the smart patch/bandage 504 is constructed on a flexible patch substrate 644. The patch substrate 644 may be constructed via three-dimensional (3D) printing. In one example embodiment, a high-capacity energy storage unit 608 stores electrical power for the smart patch/bandage 504 and is charged by a high frequency RF communication and charging pad 612. The communication and charging pad 612 enables charging and wireless communication with a microprocessor 616 via an RF signal. Power from the high-capacity energy storage unit 608 is regulated by a voltage regulator 620. A Bluetooth Low Energy (BLE) module 636 enables Bluetooth communication between the microprocessor 616 and/or the microcontroller 628, and other medical devices. A low frequency RF coupling and communication pad 640 enables communication between the microprocessor 616 and/or the microcontroller 628, and other medical devices. Memory 632 stores, for example, programs and data for the smart patch/bandage 504.

Inertia sensors or IMU (inertia measurement units) 624 are self-contained systems that measure linear and angular motion. This is conventionally accomplished with a triad of gyroscopes and triad of accelerometers. The inertia sensors and IMUs 624 collect the signals of body motion, body posture, and the like. The microprocessor 616 executes various programs and an algorithm for processing data and managing, controlling, and communicating with devices of the medical device system. In addition, the microcontroller 628 is a processing device optimized to control and interact with electronic devices, such as the inertia sensors and IMUs 624. In one example embodiment, the microcontroller 628 is implemented as a single integrated circuit dedicated to performing a particular task and executing one specific application for, for example, a corresponding device. It is noted that the inertia sensors and IMUs 624 are used primarily for movement detection applications and can be replaced or augmented with other types of sensors, such as temperature sensors, humidity sensors, and the like. Similarly, the BLE module 636 can be replaced or augmented with other types of modules, such as modules for Wi-Fi, Zigbee, and other radio frequency technologies.

Figure 7:
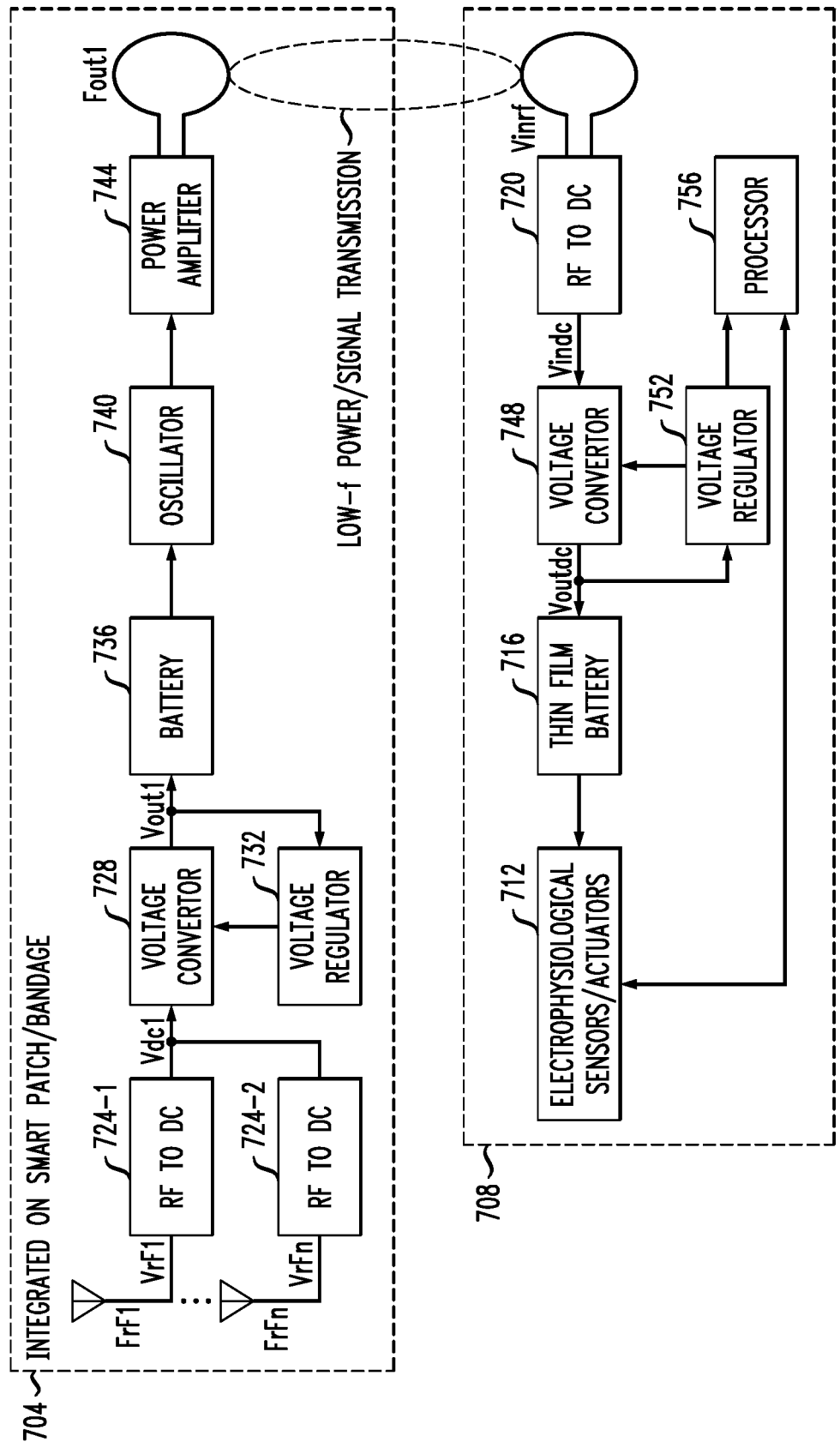
FIG. 7 is a block diagram of a smart patch/bandage and an injected or implanted electrophysiological device, in accordance with an example embodiment.

FIG. 7 is a block diagram of a smart patch/bandage 704 and an injected or implanted electrophysiological device 708, in accordance with an example embodiment. Electrophysiological sensor(s) and/or stimulator(s) 712 of the injected or implanted electrophysiological device 708 are powered by, for example, a thin-film battery 716 and communicate with the smart patch/bandage 704.

The smart patch/bandage 704 generates a near field power/data transmission signal to power the electrophysiological device 708. One or more RF-to-DC converters 724-1, 724-2 convert received radio frequency signals to a direct current DC signal. The DC signal is converted to a DC voltage for charging a battery 736 by a voltage converter 728 working in conjunction with a voltage regulator 732. The battery 736 powers an oscillator 740 working in conjunction with a power amplifier 744 to generate the low-frequency power/data transmission signal.

The low-frequency power/data transmission signal from the smart patch/bandage 704 is converted to a direct current (DC) signal by an RF-to-DC converter 720. The DC signal is converted to a DC voltage for charging the thin-film battery 716 by a voltage converter 748 working in conjunction with a voltage regulator 752. The loop antenna used for power transmission may also be used for data communications with a processor 756 to, for example, relay information to and/or from the electrophysiological sensor(s) and/or stimulator(s) 712. For low data rate communications, the communication circuit can be similar to the power transmission circuit. For high data bandwidth communication, higher radio frequencies can be used. In the latter case, the RF-to-DC converter 720 can be omitted for data communications.

Note that element 704 in FIG. 7 is wireless. There are two "tethered" cases in one or more exemplary embodiments.

Referring to FIG. 4, the subdermal hub 312 can be tethered to an implanted sensor/device 432, 436, 440. Further, the wearable server 316 can be tethered to another satellite smart pad 320T/sensor/device. In general, there can be wires running inside the human body or outside the human body, but preferably not through human skin, because that is where infection can happen. One or more embodiments advantageously reduce or eliminate a need for through-skin wiring. An on-skin device tethered to the server can simply replace the wireless components with wired connections.

Figure 8:
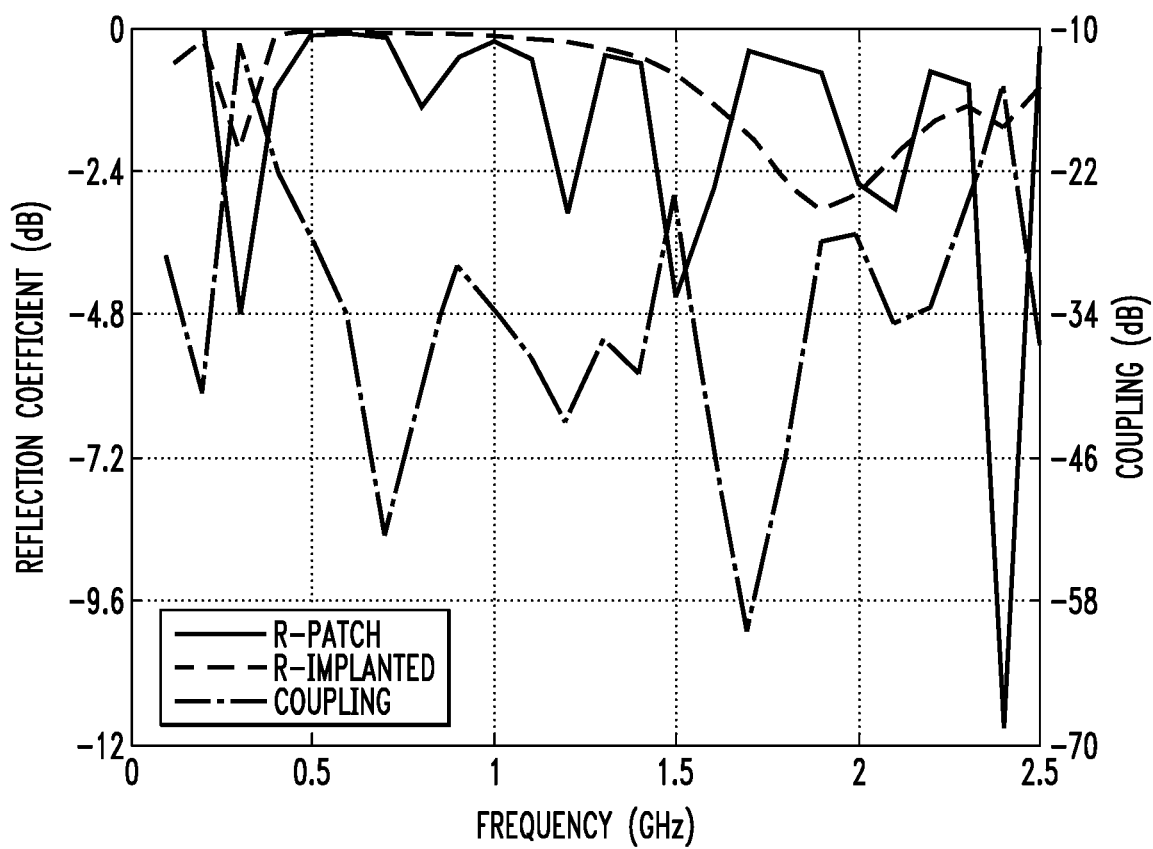
FIG. 8 is a graph of the reflection coefficient and coupling (in decibels (dB)) vs. Frequency (in GHz) produced by an electromagnetic simulation for coupling through body fluid.

FIG. 8 is a graph of the reflection coefficient and coupling (in decibels (dB)) vs. Frequency (in GHz) produced by an electromagnetic simulation for coupling through body fluid. For a saline environment, the strongest coupling is about −10.5 dB at 300 MHz. Bluetooth, for example, is based on 2.45 GHz frequency, but this frequency is strongly attenuated by water. Considering that the human body is about 70% water, the required amplification of the Bluetooth signal will consume a lot of battery power for implant devices and require more frequent recharging.

Figure 9A:
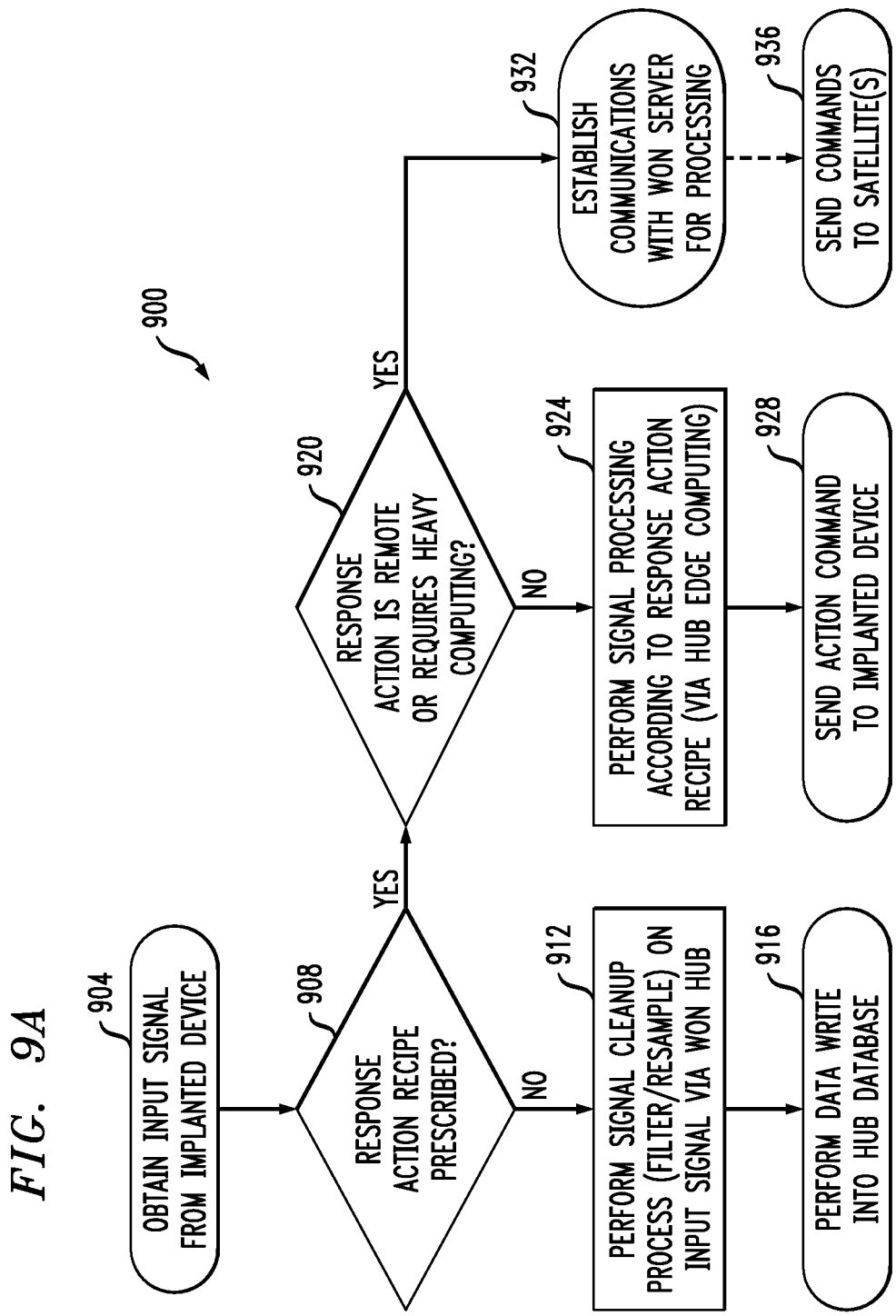
FIG. 9A is a flowchart for an example method for signal processing on a subdermal wideband on-body network (WON) hub, in accordance with an example embodiment.

FIG. 9A is a flowchart for an example method 900 for signal processing on a subdermal wideband on-body network (WON) hub 312, in accordance with an example embodiment. In one example embodiment, an input signal is obtained from an in-body medical device (operation 904). A check is performed to determine if a response action is prescribed in response to the obtained input signal (operation 908). If a response action is not prescribed in response to the obtained input signal (NO branch of operation 908), a signal cleanup process (such as filtering, resampling, and the like) is performed (operation 912) and the resulting data is written into a database of the WON hub 312 (operation 916). If a response action is prescribed in response to the obtained input signal (YES branch of operation 908), a check is performed to determine if the response action is to be performed remotely or requires heavy computing (operation 920).

If the response action is remote or requires heavy computing (YES branch of operation 920), communication is established with the WON server 316 for processing the input signal (operation 932) and commands necessitated by the processing are sent to the appropriate satellites (operation 936). If the response action is not remote and does not require heavy computing (NO branch of operation 920), signal processing is performed according to the response action recipe by the corresponding WON hub 312 (operation 924) and action commands necessitated by the processing are sent to the appropriate in-body medical device (operation 928). Given the teachings herein, the skilled artisan will understand that "heavy" computing is that more appropriately done on the server based on the relative computational capabilities of the components.

Figure 9B:
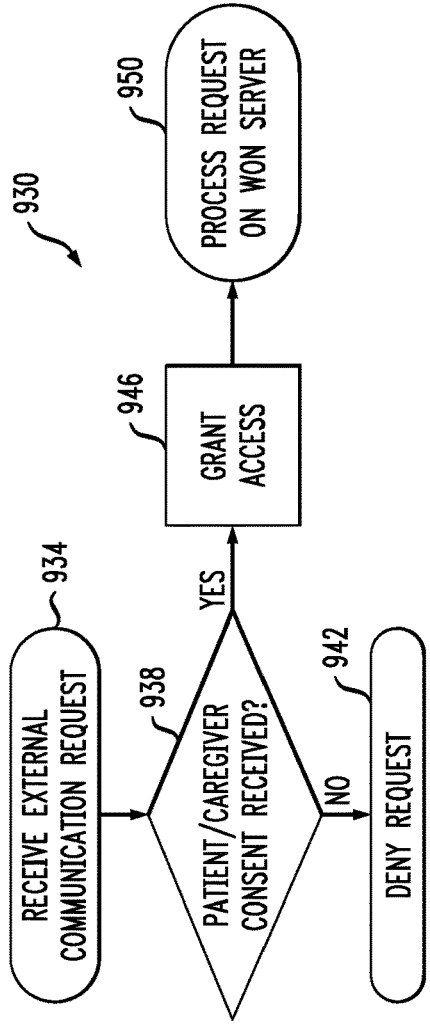
FIG. 9B is a flowchart for an example method to perform local human authentication for remote initiated requests on a wearable WON server, in accordance with an example embodiment.

FIG. 9B is a flowchart for an example method 930 to perform local human authentication for remote initiated requests on a wearable WON server 316, in accordance with an example embodiment. The security process of method 930 covers but is not limited to a doctor prescribing a new signal-response recipe and medical system update; a manufacturer firmware upgrade; a review of data and patient history by researchers and physicians; and the like. In one example embodiment, a communication request is received from an external source, such as the local medical computer 404 (operation 934). A check is performed to determine if consent has been received from the patient, a caregiver, and the like (operation 938). If consent has not been received (NO branch of operation 938), the communication request is denied (operation 942). If consent has been received (YES branch of operation 938), the communication request is granted (operation 946) and the request is processed by, for example, the WON server 316 (operation 950).

Figure 9C:
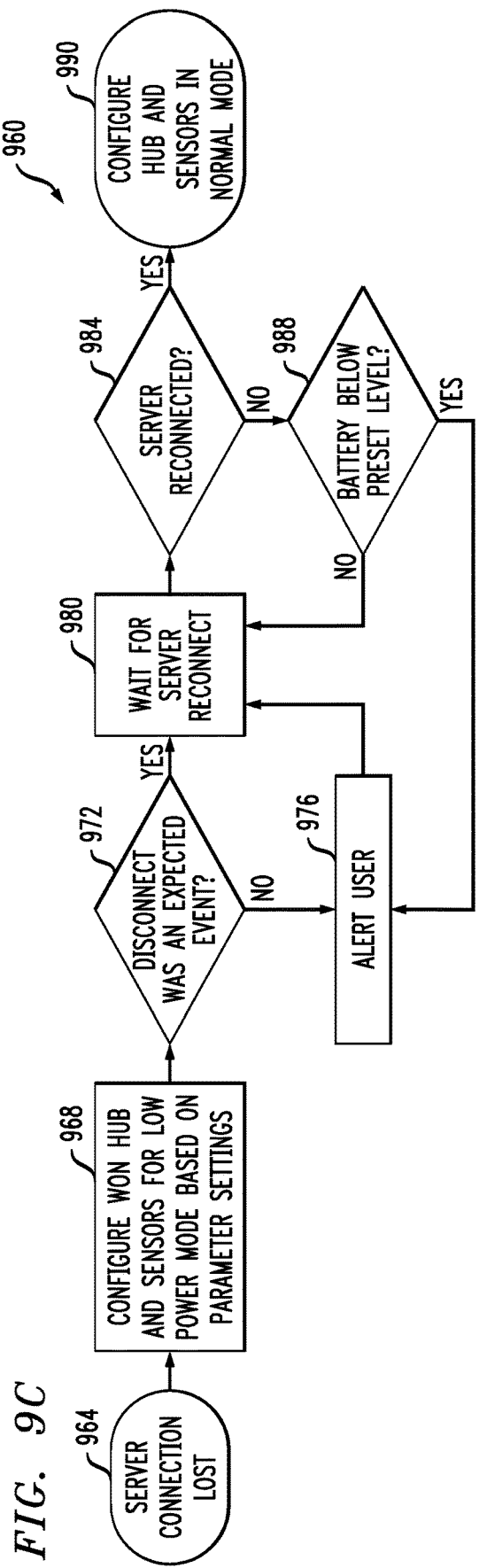
FIG. 9C is a flowchart for an example method for configuring a WON hub to operate independent of a WON server, in accordance with an example embodiment.

FIG. 9C is a flowchart for an example method 960 for configuring a WON hub 312 to operate independent of a WON server 316, in accordance with an example embodiment. For example, a connection between the WON hub 312 and the WON server 316 may be lost (as indicated in block 964) due to a network error, due to a scheduled procedure (such as an MRI exam), and the like. Regardless of the cause, the WON hub 312 and corresponding sensors are configured for a low-power mode (operation 968) and a check is performed to determine if the disconnect was for an expected event, such as a scheduled MRI exam (operation 972). If the disconnect was for an expected event (YES branch of operation 972), the WON hub 312 waits for a reconnect with the WON server 316 (operation 980). If the disconnect was not for an expected event (NO branch of operation 972), an alert is issued to the user (operation 976) and the method 960 proceeds with operation 980 where the WON hub 312 waits for the reconnect with the WON server 316. Given the teachings herein, the skilled artisan will understand that "low" power mode is one appropriate to conserve power when connectivity is lost.

During the disconnect period, a check is periodically performed to determine if the connection with the WON server 316 has been re-established (operation 984). If the connection with the WON server 316 has not been re-established (NO branch of operation 984), a check is performed to determine if the battery is below a preset level (operation 988). If the battery is not below the preset level (NO branch of operation 988), the WON hub 312 waits for the reconnect with the WON server 316 (operation 980). If the battery is below the preset level (YES branch of operation 988), an alert is issued to the user (operation 976) and the method 960 proceeds with operation 980 where the WON hub 312 waits for the reconnect with the WON server 316.

If the connection with the WON server 316 has been re-established (YES branch of operation 984), the WON hub 312 and corresponding sensors are configured for the normal mode of operation (operation 990).

Example 1

In a first example, neuro commands are collected by probes in the brain and/or spinal cord, and transmitted to the nearby WON Hub 312. In one example embodiment, some of the decoding steps (such as filtering and spike sorting) are performed by an edge computing device in the probing subsystem or WON hub 312. In one example embodiment, the raw signal will be transmitted out of body to the WON server 316 for the decoding operation. Then the decoded neuro signals (e.g., grasp right hand) will be passed to the appropriate neural application microservices (e.g., a hand movement service) under the control of a service orchestrator (a software entity residing on the WON server 316; the skilled artisan, given the teachings herein, can write suitable code), to adjust target stimulation parameters or invoke stimulation actions. The resulting action signals will travel through the WON network to the target WON satellite 320W, 320T, and are then applied to the target actuator device in the muscles or end organ.

Example 2

In a second example, biomarker sensors (such as sensors for impedance biomarkers of inflammation) and therapeutic components (such as electrical stimulation devices) can be deployed at or near an injury area where they will be powered by and communicating with a nearby implanted WON hub 312 via in-body leads. A tethered WON satellite 320T will stick on skin above the implant location of the WON hub 312 (outside of the body), as a bridge to connect the WON hub 312 with the WON server 316. The computing requirement for these tasks (for example, comparing local body temperature with a set value every second) in most cases will be light enough for them to run on the WON hub 312 directly. So, the WON server 316, in this case, is serving the purpose of transferring the biomarker information out for a medical team to monitor and support treatment decisions, and to transfer parameter adjustment commands and external data such as the phasic imaging outcome measurements back to the WON hub 312 to adjust the therapeutic and analysis routines.

Example 3

In most applications, the WON server 316 hosts and runs most of the therapeutic applications, analysis routines and other computational tasks of the medical device system. Some pertinent tasks are deployed to the WON hub 320T, 320W so that the routines can be kept running when a WON server 316 is not present, for example, when the WON server 316 was removed by accident, or during MRI scans when the WON server 316 is purposefully removed. If a certain significant task is not feasible to run on the WON hub 316 for a long time with current battery technology, a backup option is to create a long MRI scan-safe cable to allow the WON server 316 to stay outside the MRI coil while keeping the connection with WON hub 312.

The therapeutic applications, analysis routines and external data, such as the phasic imaging outcomes measurements, can be loaded into the WON server 316 directly from the WON cloud platform (if an internet connection is available). If a connection to the cloud is not available, the therapeutic applications, analysis routines and external data can be loaded via Bluetooth or universal serial bus (USB) cables from another medical computer or handheld device. In one or more embodiments, the WON server 316 is also available with preloaded therapeutic applications and analysis routines to support immediate usage in extremely harsh situations, where the parameters can be adjusted via a user interface.

Given the discussion thus far, it will be appreciated that, in general terms, an exemplary method for processing an input signal from a medical device, according to an aspect of the invention, includes the operations of obtaining the input signal from the medical device (operation 904); determining if a response action is prescribed in response to the obtained input signal (operation 908); performing a signal cleanup process (operation 912) and writing resulting data into a database of a WON hub 312 (operation 916) based on the response action not being prescribed in response to the obtained input signal; and determining a status of the response action (operation 920) based on the response action being prescribed in response to the obtained input signal.

In one example embodiment, communication with a WON server 316 is established for processing the input signal (operation 932) and commands are sent to appropriate satellites (operation 936) in response to determining that the response action is remote or requires heavy computing. In one example embodiment, signal processing is performed according to the response action recipe by the corresponding WON hub 312 (operation 924) and action commands are sent to an appropriate in-body medical device (operation 928) in response to determining that the response action is not remote and heavy computing is not required. In one example embodiment, the signal cleanup process comprises at least one of filtering and resampling.

In one aspect, a medical system for interfacing at least one in-body medical device (broadly defined to include sensors and actuators 432, 436, 440, 424) with at least one external network includes at least one subdermal wideband on-body network (WON) hub 312. The at least one subdermal wideband on-body network hub 312 includes a hub rechargeable battery, a hub processor coupled to the hub rechargeable battery, a device interface (such as in-body leads or less than 20 MHz or 300 MHz to 1 GHz radio frequency signal) configured to communicate with the at least one in-body medical device, and coupled to the hub processor, and a hub-satellite near field communications wireless interface (such as loop antenna and associated circuitry) coupled to the hub processor. Note that device 708 in FIG. 7 is a sensor, but is also representative of the hub because of the NFC coupling to the satellite. Note processor 756 and battery 716.

Figure 10:
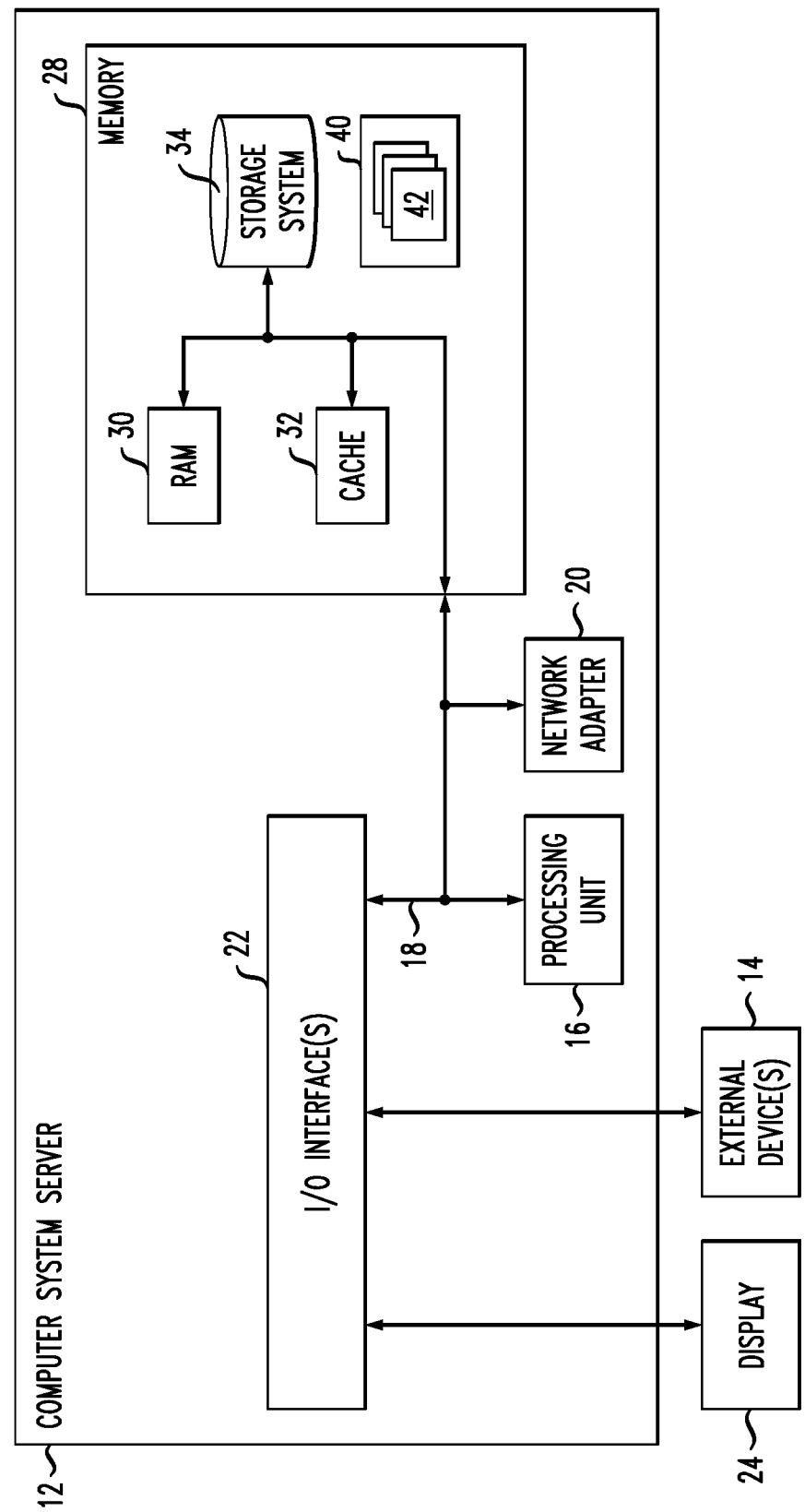
FIG. 10 depicts a computer system that may be useful in implementing one or more aspects and/or elements of the invention, also representative of a cloud computing node according to an embodiment of the present invention.

The system also includes at least one wearable wideband on-body network (WON) server 316. The at least one wearable wideband on-body network (WON) server includes a server processor, a server-satellite interface (such as a cable or wireless 2.4/5 GHz) coupled to the server processor, and an external network interface (such as Wi-Fi/4G/5G/BLE) coupled to the server processor. FIG. 10 generally represents such a server. The system still further includes at least one skin-mountable wideband on-body network (WON) tethered satellite 320T. The at least one skin-mountable wideband on-body network (WON) tethered satellite 320T includes a wired satellite-server interface (e.g., cable), coupled to the at least one wearable wideband on-body network (WON) server, and a tethered satellite near-field communications wireless interface, configured to communicate with the hub-satellite near field communications wireless interface, and coupled to the wired satellite-server interface. A software controller is implemented on at least one of the subdermal wideband on-body network (WON) hub and the wearable wideband on-body network (WON) server and is configured to monitor and control the at least one in-body medical device. Exemplary software routines for various components are discussed with regard to FIGS. 9A-9C. Wireless and tethered on-skin devices are discussed elsewhere herein.

In one example embodiment, the at least one in-body medical device includes at least first and second devices, and the device interface of the at least one subdermal wideband on-body network (WON) hub is configured to communicate with the first device. The system further includes at least one skin-mountable wideband on-body network (WON) wireless satellite 320W, and the at least one skin-mountable wideband on-body network (WON) wireless satellite 320W includes a wireless satellite-server interface (such as a 2.4/5 GHz radio frequency signal) coupled to the at least one wearable wideband on-body network (WON) server and a wireless satellite near-field communications wireless interface, coupled to the wireless satellite-server interface, and configured to communicate with the second device.

In one example embodiment, the at least one skin-mountable wideband on-body network (WON) wireless satellite, the at least one wearable wideband on-body network (WON) server, and the at least one skin-mountable wideband on-body network (WON) tethered satellite cooperatively form a mesh network. In one example embodiment, the wearable wideband on-body network (WON) server further comprises a local data storage and a user interface (UI), and is configured to provide computing services for the medical system. In one example embodiment, at least one of the skin-mountable wideband on-body network (WON) wireless satellite and the skin-mountable wideband on-body network (WON) tethered satellite comprises a smart bandage. In one example embodiment, the skin-mountable wideband on-body network (WON) tethered satellite is configured to attach to skin above a location of the at least one subdermal wideband on-body network (WON) hub. In one example embodiment, the hub-satellite near field communications wireless interface, the tethered satellite near-field communications wireless interface, and the wireless satellite near-field communications wireless interface are configured to provide data communication and charging at less than 20 MHz or in a range from 300 MHz to 1 GHz.

In one example embodiment, the at least one subdermal wideband on-body network (WON) hub is configured to provide common infrastructure functions to support implant operations, the implant operations comprising power, communication channels to out-of-body medical devices, signal buffering, and data compression and encryption. In one example embodiment, the at least one subdermal wideband on-body network (WON) hub comprises a flexible substrate (i.e., conformable to the skin surface as will be familiar to the skilled artisan) and is further configured to provide edge computing functionality and standard communication ports for communication with at least the first device. In one example embodiment, a local medical computer 404 is coupled to the external network interface and configured to communicate with cloud services, monitor biomarkers, adjust parameters, and provision a therapeutic application library. In one example embodiment, the device interface of the at least one subdermal wideband on-body network (WON) hub is configured to communicate with the first device via a wired communication path. In one example embodiment, the device interface of the at least one subdermal wideband on-body network (WON) hub is configured to communicate with the first device wirelessly at less than 20 MHz or in a range from 300 MHz to 1 GHz.

In one aspect, an on-skin patch 504 comprises a flexible patch substrate 644; (optionally, one or more sensor devices 624 secured to the flexible patch substrate or the sensors can be external); a hardware processor 616, 628 secured to the flexible patch substrate and configured to obtain information from the one or more sensor devices 624; a battery 736 secured to the flexible patch substrate 644 and configured to provide power to components of the on-skin patch 504; one or more radio frequency to direct current (RF-to-DC) converters 724-1, 724-2 secured to the flexible patch substrate 644 and configured to convert a received radio frequency signal to a direct current (DC) signal; a voltage converter 728 and a voltage regulator 732 secured to the flexible patch substrate 644 and configured to convert the direct current (DC) signal to a direct current (DC) voltage to charge the battery 736; and an oscillator 740 and a power amplifier 744 secured to the flexible patch substrate 644 and configured to generate a low-frequency power/data transmission signal.

In one example embodiment, the on-skin patch 504 is configured to communicate with a re-usable electronics module. In one example embodiment, at least one of the sensor devices 624 is one of a heater/thermometer device and a potential of hydrogen (pH) sensor array. In one example embodiment, a low frequency radio frequency (RF) coupling and communication pad 640 is configured to provide communication with the hardware processor 616, 628. The patch substrate 644 can be constructed, for example, via three-dimensional (3D) printing.

One or more embodiments of the invention, or elements thereof, can be implemented in the form of an apparatus including a memory and at least one processor that is coupled to the memory and operative to perform exemplary method steps. FIG. 10 depicts a computer system that may be useful in implementing one or more aspects and/or elements of the invention, also representative of a cloud computing node according to an embodiment of the present invention. Referring now to FIG. 10, cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 10, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, and external disk drive arrays, RAID systems, tape drives, and data archival storage systems, etc.

Thus, one or more embodiments can make use of software running on a general purpose computer or workstation. With reference to FIG. 10, such an implementation might employ, for example, a processor 16, a memory 28, and an input/output interface 22 to a display 24 and external device(s) 14 such as a keyboard, a pointing device, or the like. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory) 30, ROM (read only memory), a fixed memory device (for example, hard drive 34), a removable memory device (for example, diskette), a flash memory and the like. In addition, the phrase "input/output interface" as used herein, is intended to contemplate an interface to, for example, one or more mechanisms for inputting data to the processing unit (for example, mouse), and one or more mechanisms for providing results associated with the processing unit (for example, printer). The processor 16, memory 28, and input/output interface 22 can be interconnected, for example, via bus 18 as part of a data processing unit 12. Suitable interconnections, for example via bus 18, can also be provided to a network interface 20, such as a network card, which can be provided to interface with a computer network, and to a media interface, such as a diskette or CD-ROM drive, which can be provided to interface with suitable media.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 16 coupled directly or indirectly to memory elements 28 through a system bus 18. The memory elements can include local memory employed during actual implementation of the program code, bulk storage, and cache memories 32 which provide temporary storage of at least some program code in order to reduce the number of times code must be retrieved from bulk storage during implementation.

Input/output or I/O devices (including but not limited to keyboards, displays, pointing devices, and the like) can be coupled to the system either directly or through intervening I/O controllers.

Network adapters 20 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 12 as shown in FIG. 10) running a server program. It will be understood that such a physical server may or may not include a display and keyboard.

One or more embodiments can be at least partially implemented in the context of a cloud or virtual machine environment, although this is exemplary and non-limiting. Reference is made back to FIGS. 1-2 and accompanying text as well as discussion of elements 96 and 508.

It should be noted that any of the methods described herein can include an additional step of providing a system comprising distinct software modules embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described. The method steps can then be carried out using the distinct software modules and/or sub-modules of the system, as described above, executing on one or more hardware processors such as 16. Further, a computer program product can include a computer-readable storage medium with code adapted to be implemented to carry out one or more method steps described herein, including the provision of the system with the distinct software modules.

One example of user interface that could be employed in some cases is hypertext markup language (HTML) code served out by a server or the like, to a browser of a computing device of a user. The HTML is parsed by the browser on the user's computing device to create a graphical user interface (GUI).

Exemplary System and Article of Manufacture Details

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A medical system for interfacing at least one in-body medical device with at least one external network, comprising:
    at least one subdermal wideband on-body network (WON) hub, the at least one subdermal wideband on-body network hub comprising a hub rechargeable battery, a hub processor coupled to the hub rechargeable battery, a device interface configured to communicate with the at least one in-body medical device, and coupled to the hub processor, and a hub-satellite near field communications wireless interface coupled to the hub processor;
    at least one wearable wideband on-body network (WON) server, the at least one wearable wideband on-body network (WON) server comprising a server processor, a server-satellite interface coupled to the server processor, and an external network interface coupled to the server processor;
    at least one skin-mountable wideband on-body network (WON) tethered satellite, the at least one skin-mountable wideband on-body network (WON) tethered satellite comprising a wired satellite-server interface, coupled to the at least one wearable wideband on-body network (WON) server, and a tethered satellite near-field communications wireless interface, configured to communicate with the hub-satellite near field communications wireless interface, and coupled to the wired satellite-server interface; and
    a software controller implemented on at least one of the subdermal wideband on-body network (WON) hub and the wearable wideband on-body network (WON) server and configured to monitor and control the at least one in-body medical device.

2. The medical system of claim 1, wherein the at least one in-body medical device includes at least first and second devices, wherein the device interface of the at least one subdermal wideband on-body network (WON) hub is configured to communicate with the first device, further comprising at least one skin-mountable wideband on-body network (WON) wireless satellite, the at least one skin-mountable wideband on-body network (WON) wireless satellite comprising a wireless satellite-server interface coupled to the at least one wearable wideband on-body network (WON) server and a wireless satellite near-field communications wireless interface, coupled to the wireless satellite-server interface, and configured to communicate with the second device.

3. The medical system of claim 2, wherein the at least one skin-mountable wideband on-body network (WON) wireless satellite, the at least one wearable wideband on-body network (WON) server, and the at least one skin-mountable wideband on-body network (WON) tethered satellite cooperatively form a mesh network.

4. The medical system of claim 3, wherein the wearable wideband on-body network (WON) server further comprises a local data storage and a user interface (UI), and is configured to provide computing services for the medical system.

5. The medical system of claim 3, wherein at least one of the skin-mountable wideband on-body network (WON) wireless satellite and the skin-mountable wideband on-body network (WON) tethered satellite comprises a smart bandage.

6. The medical system of claim 3, wherein the skin-mountable wideband on-body network (WON) tethered satellite is configured to attach to skin above a location of the at least one subdermal wideband on-body network (WON) hub.

7. The medical system of claim 3, wherein the hub-satellite near field communications wireless interface, the tethered satellite near-field communications wireless interface, and the wireless satellite near-field communications wireless interface are configured to provide data communication and charging at less than 20 MHz or in a range from 300 MHz to 1 GHz.

8. The medical system of claim 3, wherein the at least one subdermal wideband on-body network (WON) hub is configured to provide common infrastructure functions to support implant operations, the implant operations comprising power, communication channels to out-of-body medical devices, signal buffering, and data compression and encryption.

9. The medical system of claim 8, wherein the at least one subdermal wideband on-body network (WON) hub comprises a flexible substrate and is further configured to provide edge computing functionality and standard communication ports for communication with at least the first device.

10. The medical system of claim 3, further comprising a local medical computer 404 coupled to the external network interface and configured to communicate with cloud services, monitor biomarkers, adjust parameters, and provision a therapeutic application library.

11. The medical system of claim 3, wherein the device interface of the at least one subdermal wideband on-body network (WON) hub is configured to communicate with the first device via a wired communication path.

12. The medical system of claim 3, wherein the device interface of the at least one subdermal wideband on-body network (WON) hub is configured to communicate with the first device wirelessly at less than 20 MHz or in a range from 300 MHz to 1 GHz.

* * * * *